(12) United States Patent
He et al.

(10) Patent No.: US 7,309,387 B2
(45) Date of Patent: Dec. 18, 2007

(54) METHODS AND APPARATUS FOR A LOW-PROFILE AIR PURIFIER

(75) Inventors: Mengtao Pete He, Scottsdale, AZ (US); Paul Pappalardo, Scottsdale, AZ (US); Winston Uchiyama, Scottsdale, AZ (US); Carl Triplett, Scottsdale, AZ (US)

(73) Assignee: The Dial Corporation, Scottsdale, AZ (US)

( * ) Notice: Subject to any disclaimer, the term of this patent is extended or adjusted under 35 U.S.C. 154(b) by 161 days.

(21) Appl. No.: 11/161,868

(22) Filed: Aug. 19, 2005

(65) Prior Publication Data

US 2006/0075729 A1  Apr. 13, 2006

Related U.S. Application Data

(60) Provisional application No. 60/603,093, filed on Aug. 20, 2004.

(51) Int. Cl.
*B01D 39/00* (2006.01)

(52) U.S. Cl. .......................... 96/223; 55/467; 55/471; 55/472; 261/DIG. 88; 261/DIG. 89; 96/222

(58) Field of Classification Search .............. 55/471, 55/467, 472; 96/222, 223; 261/DIG. 88, 261/DIG. 89
See application file for complete search history.

(56) References Cited

U.S. PATENT DOCUMENTS

| | | | |
|---|---|---|---|
| 4,795,883 A * | 1/1989 | Glucksman et al. | 392/390 |
| 4,804,821 A * | 2/1989 | Glucksman | 392/390 |
| 5,465,198 A * | 11/1995 | Kellogg | 362/253 |
| 5,578,113 A | 11/1996 | Glenn | |
| 5,601,636 A * | 2/1997 | Glucksman | 96/63 |
| 5,658,130 A | 8/1997 | Goldstein et al. | |
| 5,660,605 A | 8/1997 | Chan et al. | |
| D403,417 S | 12/1998 | Rakocy | |
| 5,893,939 A | 4/1999 | Rakocy et al. | |
| 5,997,674 A | 12/1999 | Rakocy et al. | |
| 6,116,246 A | 9/2000 | Glenn et al. | |
| 6,315,821 B1 | 11/2001 | Pillion et al. | |
| 6,328,791 B1 | 12/2001 | Pillion et al. | |
| 6,413,302 B1 * | 7/2002 | Harrison et al. | 96/63 |
| 6,447,587 B1 | 9/2002 | Pillion et al. | |
| 6,478,440 B1 | 11/2002 | Jaworski et al. | |
| 6,494,940 B1 | 12/2002 | Hak | |

(Continued)

FOREIGN PATENT DOCUMENTS

EP  1 283 062  2/2003

(Continued)

*Primary Examiner*—Duane Smith
*Assistant Examiner*—Sonji Turner
(74) *Attorney, Agent, or Firm*—Snell & Wilmer LLP

(57) ABSTRACT

An air purifier having dimensions that enable the air purifier to be more discrete is disclosed. The air purifier also includes components that enable the air purifier to mimic a particular environment in which the air purifier may be placed. In addition, the air purifier includes electrical plugs such that the air purifier is able to be plugged into a traditional wall outlet and the components enable the air purifier to mimic the appearance and function of the wall outlet. Furthermore, the air purifier includes one or more modules to sanitize incoming air, facilitate air flow through the air purifier, and/or dispense scented vapors.

15 Claims, 18 Drawing Sheets

U.S. PATENT DOCUMENTS

| | | | |
|---|---|---|---|
| 6,507,282 B1 | 1/2003 | Sherwood | |
| 6,508,868 B2 | 1/2003 | Pillion et al. | |
| 6,570,139 B1 | 5/2003 | Levy et al. | |
| 6,579,333 B2 * | 6/2003 | Huang | 55/385.1 |
| 6,610,118 B2 | 8/2003 | Bryce et al. | |
| 6,645,266 B2 * | 11/2003 | Huang | 55/471 |
| 6,712,889 B2 | 3/2004 | Pillion et al. | |
| 6,714,725 B2 * | 3/2004 | Grone et al. | 392/392 |
| 6,812,437 B2 | 11/2004 | Levy et al. | |
| 6,862,403 B2 * | 3/2005 | Pedrotti et al. | 392/395 |
| 7,155,116 B2 * | 12/2006 | He et al. | 392/392 |
| 2001/0037732 A1 | 11/2001 | Pillion et al. | |
| 2002/0040642 A1 | 4/2002 | Pillion et al. | |
| 2002/0152894 A1 | 10/2002 | Pillion et al. | |
| 2003/0005668 A1 | 1/2003 | Huang | |
| 2003/0056478 A1 | 3/2003 | Pillion et al. | |
| 2003/0070544 A1 | 4/2003 | Mulvaney et al. | |
| 2003/0219240 A1 | 11/2003 | Levy et al. | |
| 2004/0079059 A1 | 4/2004 | Pillion et al. | |

FOREIGN PATENT DOCUMENTS

| | | |
|---|---|---|
| WO | WO 95/05886 | 3/1995 |
| WO | WO 98/58112 | 12/1998 |
| WO | WO 01/51169 | 7/2001 |
| WO | WO 01/51214 | 7/2001 |
| WO | WO 01/52215 | 7/2001 |
| WO | WO 01/68154 A1 * | 9/2001 |
| WO | WO 01/83080 | 11/2001 |
| WO | WO 02/26349 | 4/2002 |
| WO | WO 02/055176 | 7/2002 |
| WO | WO 03/088430 | 10/2003 |

* cited by examiner

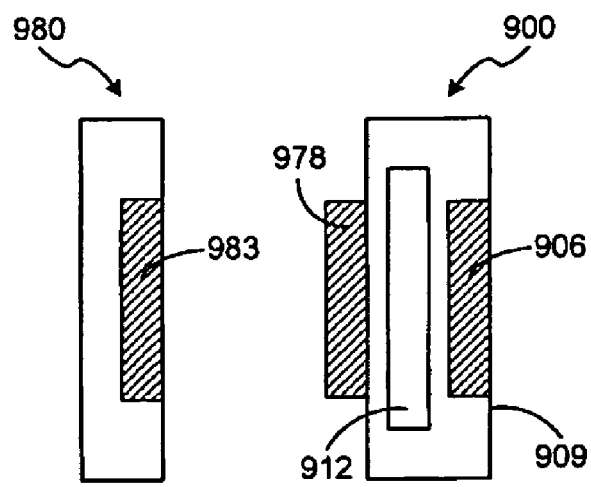
FIG. 11
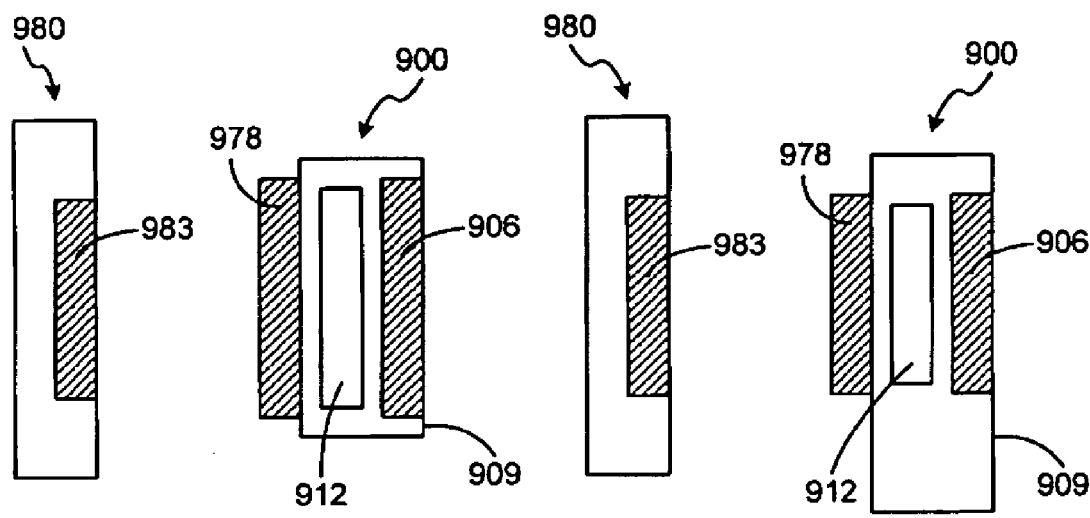
FIG. 12  FIG. 13

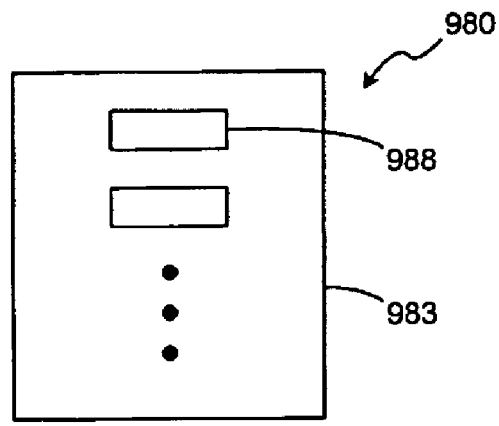
FIG. 14
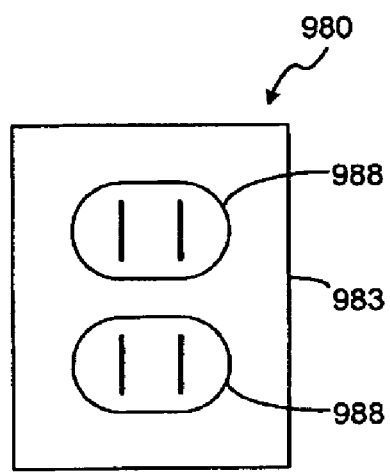 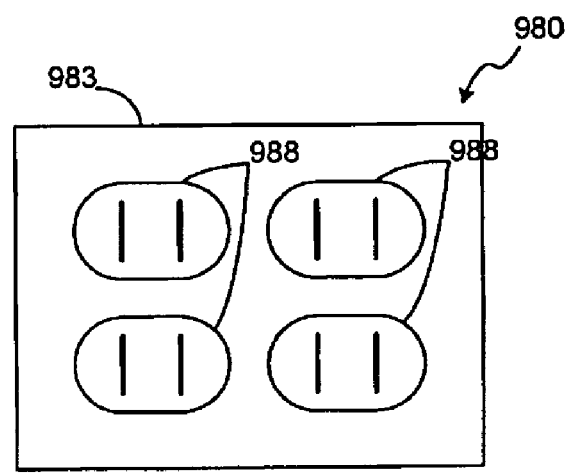
FIG. 15  FIG. 16

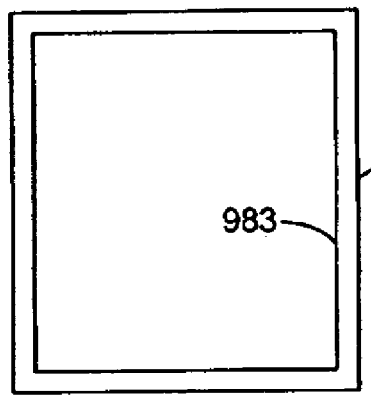
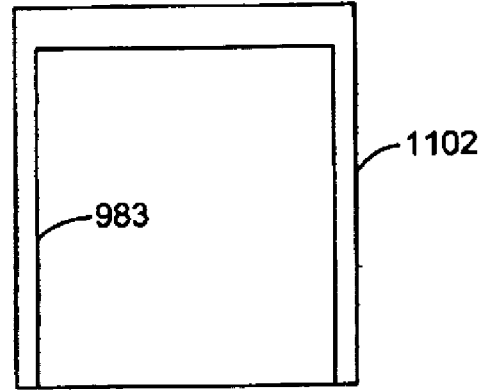
FIG. 20A  FIG. 20B
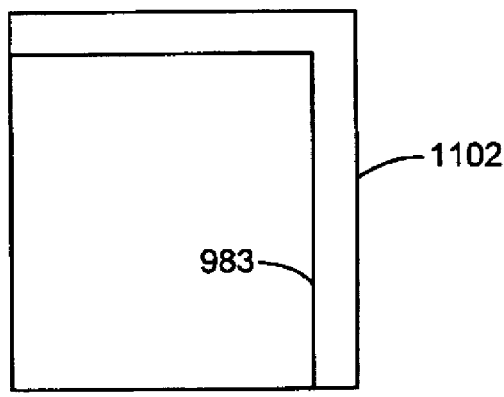
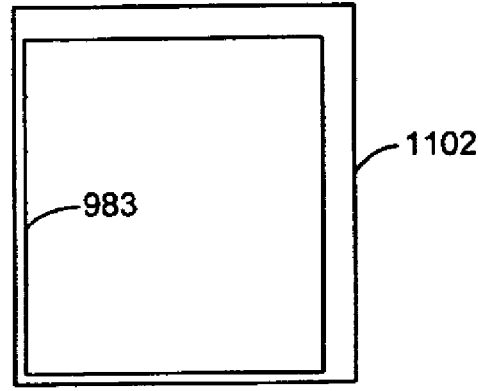
FIG. 20C  FIG. 20D

METHODS AND APPARATUS FOR A LOW-PROFILE AIR PURIFIER

CROSS-REFERENCE TO RELATED APPLICATIONS

This Application claims priority to, and the benefit of U.S. Pat. application Ser. No. 60/603,093 filed Aug. 20, 2004, wherein such provisional application is hereby incorporated, in its entirety, by reference.

FIELD OF INVENTION

The invention relates, generally, to air-purification devices and, in particular, to a low-profile air purifier configured, for example, to plug into a traditional household power outlet.

BACKGROUND OF INVENTION

In recent years there has been an increased emphasis on improving the quality of the air or "air health" of living spaces. This has in turn increased the popularity of consumer air purification systems for use in an individual's home. It is often convenient to use an available receptacle (e.g., a conventional household electrical outlet) as a source of electrical power for systems configured to perform some type of environment-altering task. Due to the location and accessibility of conventional wall outlets, and the size and shape of known devices, it is common for such devices to be relatively conspicuous when plugged into a wall outlet.

In some instances, it is desirable to enhance the extent to which vapor-dispensing devices and/or air purifiers integrate or blend in with their environment. The level of discreetness is generally related to a device's overall geometry and the manner in which the device contacts the wall and/or receptacle to which it is connected. In addition, there are instances where it is advantageous to provide an environment-altering apparatus with enhanced functional discreetness. Thus, there is a need for vapor-dispensing devices and air purifiers which do not eliminate, reduce, or otherwise alter a user's access to the functional features of the receptacle.

SUMMARY OF INVENTION

In general, the present invention provides an air purification device that is low-profile compact, or otherwise configured to integrate with its environment in a discreet manner. In general, the device includes an air sanitation module and an optional airflow module. In accordance with a further embodiment, the air purification device includes a vapor dispensing module configured to add one or more fragrances to the purified air.

The device may accomplish this discreetness in a number of ways—for example, by blending in with one or more components of the environment (e.g., a wall outlet or other surface), by covering or otherwise occluding all or a portion of the receptacle, and/or by appearing to be something other than an environment-altering device.

A low-profile air purifier configured to mimic an electrical outlet according to various exemplary embodiments of the invention includes a housing having an anterior surface with an electrical receptacle pattern substantially similar to the electrical receptacle pattern of the electrical outlet; a posterior surface including a plug pattern having at least one plug; and a device interposed between said anterior surface and said posterior surface. In one embodiment, the device is configured to intake air, purify the air, and output the purified air.

BRIEF DESCRIPTION OF THE DRAWINGS

The subject invention will hereinafter be described in conjunction with the appended drawing figures, wherein like numerals denote like elements, and:

FIG. 11 is a diagram of a side view of a vapor-dispensing device and receptacle in accordance with one embodiment of the present invention;

FIG. 12 is a diagram of a side view of a vapor-dispensing device and receptacle in accordance with another embodiment of the present invention;

FIG. 13 is a diagram of a side view of a vapor-dispensing device and receptacle in accordance with yet another embodiment of the present invention;

FIG. 14 is a diagram of a front view of an exemplary receptacle having a number of outlets;

FIG. 15 is a diagram of conventional dual-outlet receptacles;

FIG. 16 is a diagram of a conventional quad-outlet receptacle;

FIGS. 20A-20D are diagrams of various configurations of vapor-dispensing device geometries with respect to a receptacle;

DETAILED DESCRIPTION

The detailed description of exemplary embodiments of the invention herein makes reference to the accompanying figures, which show the exemplary embodiment by way of illustration. While these exemplary embodiments are described in sufficient detail to enable one skilled in the art to practice the invention, it should be understood that other embodiments may be realized, and that changes may be made without departing from the spirit and scope of the invention. Thus, the detailed description herein is presented for purposes of illustration only and not by way of limitation.

For the sake of brevity, functional embodiments of the apparatus and systems (and components of the individual operating components of the systems) may not be described in detail herein. Furthermore, the connecting lines shown in the various figures contained herein are intended to represent exemplary functional relationships and/or physical connections between the various elements. It should be noted that many alternative or additional functional relationships or physical connections may be present in a practical system.

Systems and methods in accordance with various embodiments of the present invention generally provide a low-profile air purifier configured to integrate with its environment in a discreet manner. For example, the air purifier may blend in with one or more components of the environment by covering or otherwise occluding all or a portion of the receptacle, and/or by appearing to be something other than an air purifier (e.g., an electrical outlet). Furthermore, the air purifier may include dimensions (e.g., length, width, diameter, thickness, shape, and the like) that allow the air purifier to be discrete. In other words, less noticeable than air purifiers having different dimensions.

Figure 1:
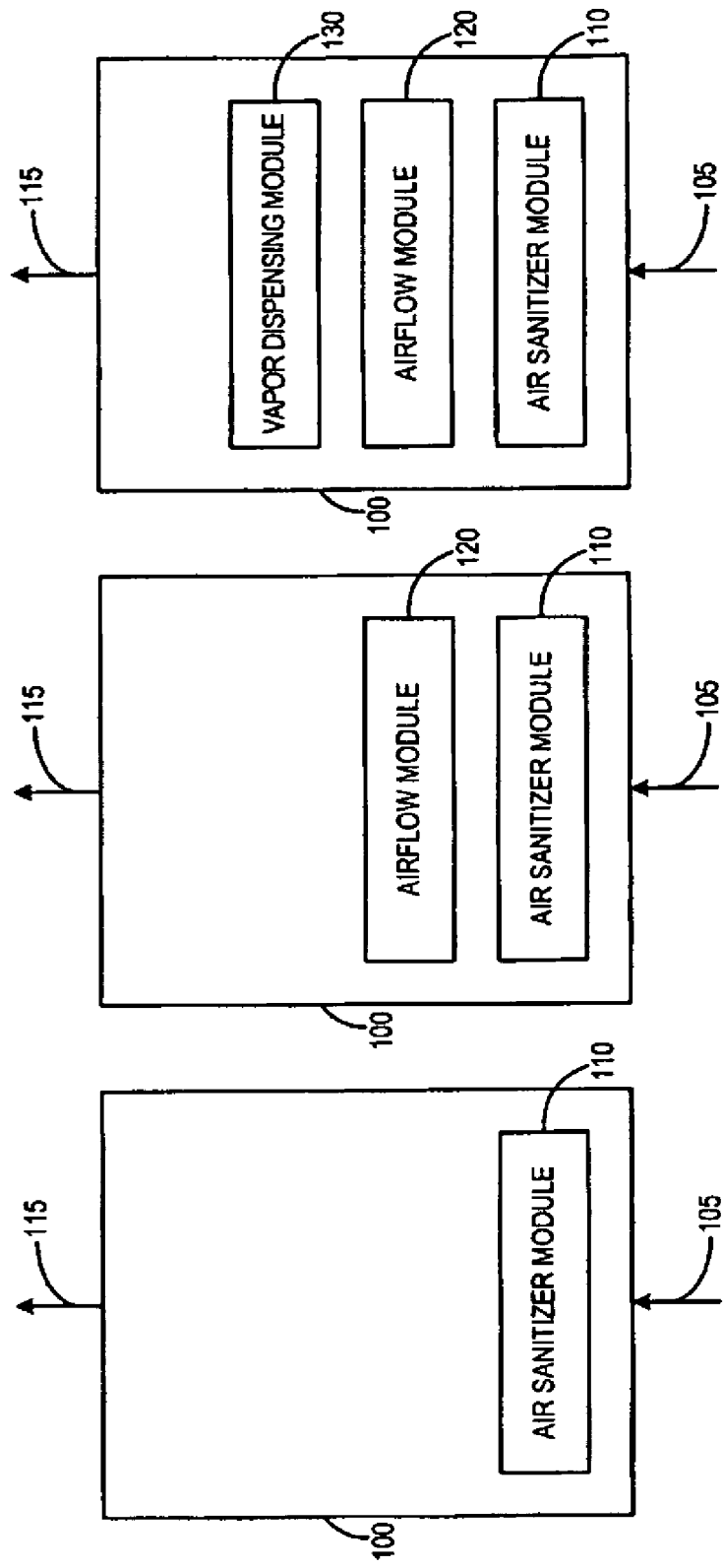
FIGS. 1A-1C are schematic block diagrams of various embodiments of the present invention.

Turning now to the figures, FIG. 1A is a block diagram of one exemplary embodiment of an air purifier 100 in accordance with the present invention. Air purifier 100 includes an air intake 105, an air sanitizer module 110, and an air output FIG. 1B is a block diagram of air purifier 100 further including an airflow module 120 in communication with air sanitizer module 110, wherein airflow module 120 is configured to push, pull, or otherwise facilitate the movement of air from air intake 105 through air sanitizer module 110, and eventually to air output 115. FIG. 1C is a block diagram illustrating yet another embodiment of air purifier 100, wherein air purifier 100 further includes a vapor dispensing module 130 configured to add one or more fragrances to the air from airflow module 120 and/or air sanitizer module 110. In other words, air purifier 100 may act such that air output 115 is fragranced and/or purified, and may also include one or more controls configured to modulate the relative degree of fragrancing and/or purification.

Air sanitizer module 110, in various embodiments, may include any device, component, or combination of components suitably configured to scrub, purify, filter, sanitize, or otherwise process incoming air to produce cleaner air as an output. In this regard, air sanitizer module 110 may be configured to address the presence of germs (e.g., bacteria, viruses, and the like), allergens (e.g., pollen, dander, lint, dust, smog, mold, and the like), and/or malodors (e.g., chemical odors, microorganism odors, and the like) produced in various environments. Notably, the term environment, as used herein, corresponds to any defined space, whether open or enclosed by one or more surfaces, walls, ceilings, floors, or other solid or fictitious boundaries. For example, environment may correspond to a residential room (e.g., bedroom, bathroom, kitchen, and the like), commercial space (e.g., factory floor, office cubicles, and the like), automotive enclosure (e.g., car, truck, recreation-vehicle, and the like), airline compartment, or any other space in which it is desirable to deliver a purified and/or fragranced air.

Airflow module 120 may include any device, component, or combination of components suitably configured to move air within and/or through air purifier 100. In this regard, airflow module 120 may include any device now known or later developed capable of causing air to move within and/or through air purifier 100.

Vapor dispensing module 130 may include any device, component, or combination of components suitably configured to add a fragrance, scent, or other vapor (e.g., insecticide) to air output by air purifier 100. Notably, the invention contemplates that air purifier 100 may include any suitable vapor dispensing technique or device now known in the art or later developed.

Figure 2:
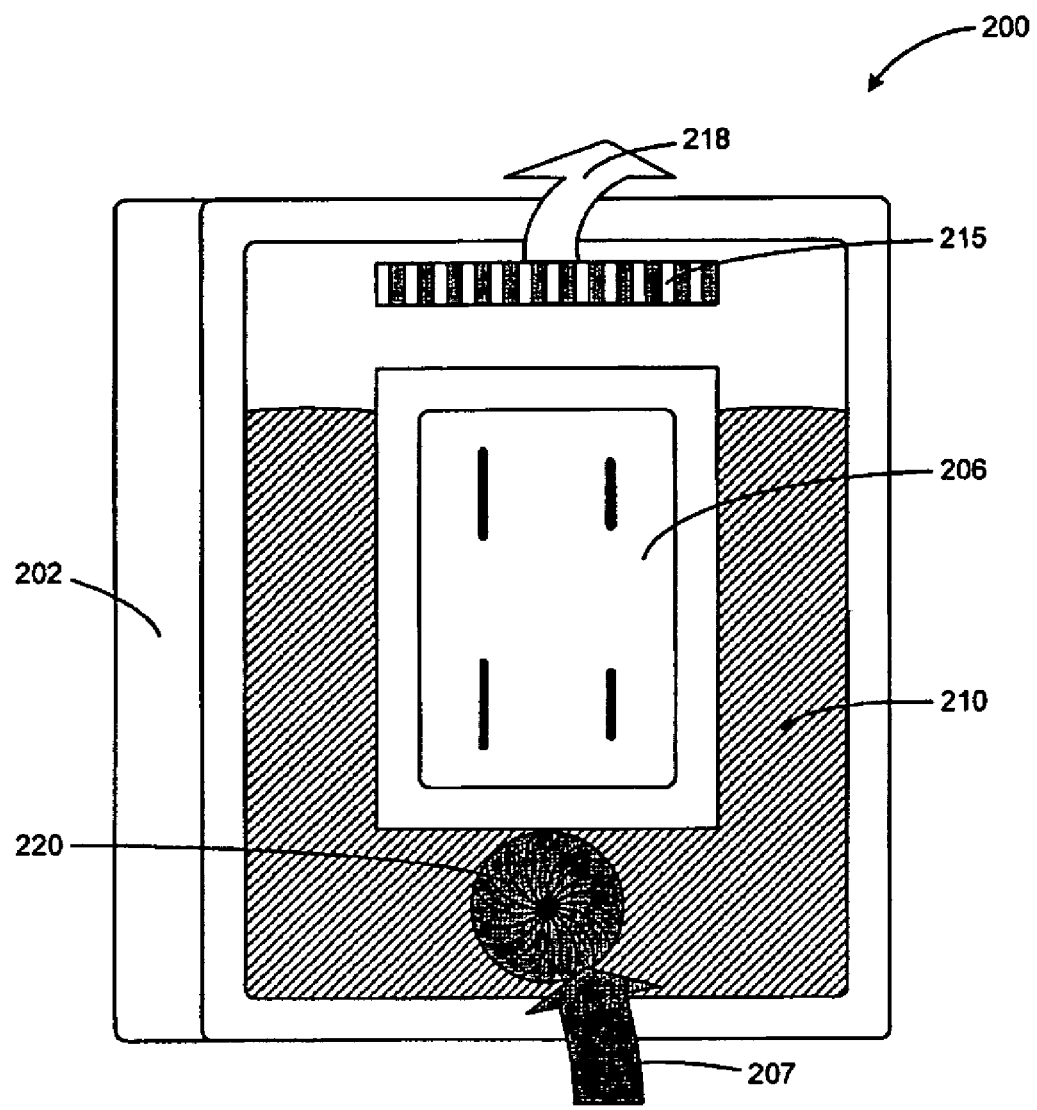
FIG. 2 is an air purifier in accordance with one embodiment of the present invention.

Air purifiers in accordance with various exemplary embodiments of the invention include components enabling the air purifier to be more discrete. For example, FIG. 2 illustrates an air purifier 200 including a low-profile housing 202, which may be formed of any material suitable for use in forming an air purifier. Examples of suitable materials for housing 202 include, but are not limited to, plastic, metal, ceramic, cermet, and the like. Furthermore, housing 202 may include a relatively small width, height, depth, and/or the like such that housing 202 is less conspicuous than it would otherwise be if housing 202 included larger dimensions. For example, housing 202 may include a width in the range of about 6 centimeters (cm) to about 14 cm, a height in the range of about 10 cm to about 20, and a depth (thickness) in the range of about 2 cm to about 7 cm, preferably 5 cm, and most preferably 3 cm.

In accordance with one embodiment of the invention, air purifier 200 includes an air intake. An air intake may be any device, component, or combination of components known in the art or developed in the future capable of allowing air 207 to move into air purifier 200. In one exemplary embodiment of the invention, an air intake includes one or more vents and/or other aperture(s) to allow air 207 to flow into air purifier 200.

Air purifier 200, in another exemplary embodiment, includes an airflow module 220 similar to airflow module 120 discussed above. In accordance with an aspect of the invention, airflow module 220 includes a fan configured to cause air 207 to flow into an air intake, and cause air 207 to move through or across at least a portion of an air sanitizer module 210 (discussed below). In accordance with various aspects of the invention, the fan may be an AC or DC micro fan, a squirrel cage fan, a cross-flow fan, and/or the like. In another exemplary embodiment, airflow module 220 includes ionization technology configured to create an active air flow through air purifier 100 via an electric field. In yet another exemplary embodiment, airflow module 220 includes a pump suitably configured to cause air 207 to flow through air purifier 200. Notably, the invention contemplates that airflow module 220 may incorporate any suitable active air flow technique or device known in the art or developed in the future.

Air sanitizer module 210 may be any device, component, or combination of components suitably configured to substantially prevent unwanted particles and/or particulates from passing through it. In other words, air sanitizer module 210 may be any device that at least partially purifies air 207 as it passes through it. In one exemplary embodiment, air sanitizer module 210 includes one or more filters to purify incoming air 207. In accordance with an aspect of one exemplary embodiment of the invention, the filter may be a fiber filter such as, for example, a high efficiency particulate air (HEPA) filter. In another aspect of the invention, the filter may be a Filtrete filter manufactured by 3M Corporation of St. Paul, Minn.

In accordance with another exemplary embodiment, air sanitizer module 210 includes one or more chemical absorbents to purify air 207. Examples of chemical absorbents include, but are certainly not limited to, carbon; baking soda; an anti-germ, chemical-reaction-type air sanitizer; and the like. In yet another exemplary embodiment, air sanitizer module 210 incorporates ultraviolet, ozonation, and/or ionization air sanitization technologies to purify air 207. Notably, the invention contemplates that air sanitizer module 210 may incorporate any technique, process, device, and/or components known in the art or developed in the future for purifying air 207.

In another exemplary embodiment, air purifier 200 includes an air output 215. In accordance with an aspect of one exemplary embodiment, air output 215 includes one or more vents and/or apertures suitably configured to output purified air 218 into the environment surrounding air purifier 200.

Air purifier 200, in one exemplary embodiment, includes an outlet pattern including one or more plug receptacles 206 suitably configured to accept one or more electrical connectors from an external electrical device (not shown). Plug receptacles 206 may be any plug receptacle known in the art capable of having an electric plug inserted within it and providing electric current to the device connected to the plug. Thus, plug receptacles 206 may be configured to function similar to standard plug receptacles found, for example, in a wall outlet or on a power strip. As such, plug receptacles 206 may also function to mimic (i.e., resemble in appearance) a standard outlet such that air purifier 200 is less likely to be detected as an air purifying device. In another embodiment of the invention, plug receptacles 206 are not functional, but are simply configured to mimic the standard outlet similar to the embodiment discussed above. Notably, air purifier 200 may include any shape and/or dimensions suitable for purifying air 207. However, embodiments desiring that air purifier 200 mimic a standard duplex wall outlet, power strip, or quadplex should include dimensions (e.g., height, width, depth, and the like) and/or shapes (e.g., rectangular, square, and the like) similar to well-accepted dimensions/shapes for these outlets and/or dimensions/shapes less likely to be otherwise noticed.

In operation, airflow module 220 causes air 207 to enter air purifier 200 via an air intake. Airflow module 220 then causes air 207 and pass over, across, and/or pass through air sanitizer module 210, wherein impurities in air 207 are trapped within air sanitizer module 210 resulting in purified air 218. Airflow module 220 forces purified air 218 to exit air purifier 200 though air output 215 to the surrounding environment.

Figure 3:
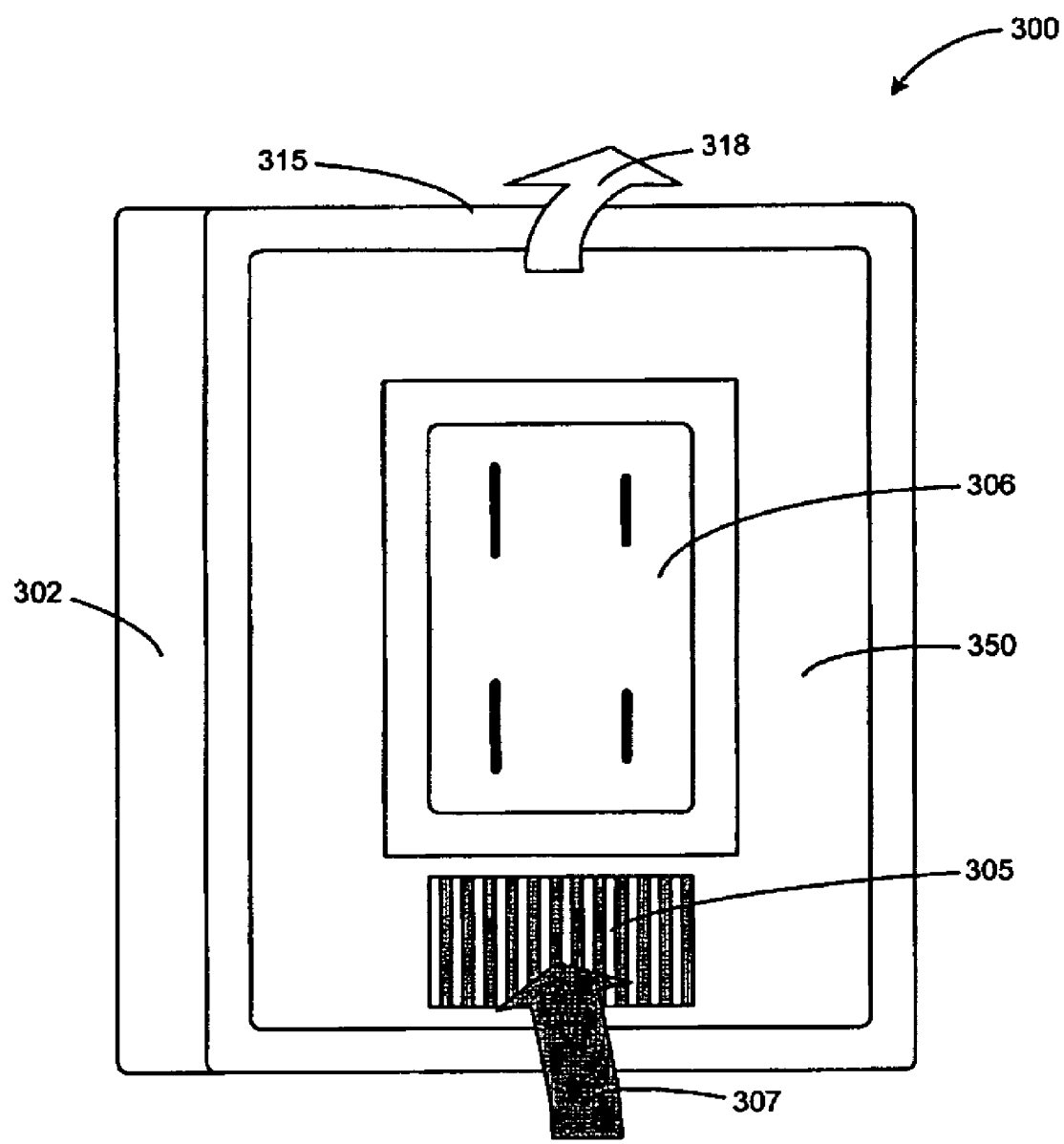
FIG. 3 is an alternate view of the air purifier shown in FIG. 2.

Another embodiment of a low-profile air purifier includes vents for facilitating air flow through the air purifier. For example, FIG. 3 illustrates an air purifier 300 including a housing 302, one or more plug receptacles 306, an air output 315 for purified air 318, and an air sanitizer module (not shown) similar to housing 202, an air intake for air 207, plug receptacles 206, air output 215 for purified air 218, and air sanitizer module 210, respectively, discussed above with reference to FIG. 2. In accordance with one exemplary embodiment of the invention, a cover 350 including air intake 305 is included a part of air purifier 300, wherein air intake 305 includes vents for allowing air 307 to enter air purifier 300.

Figure 4:
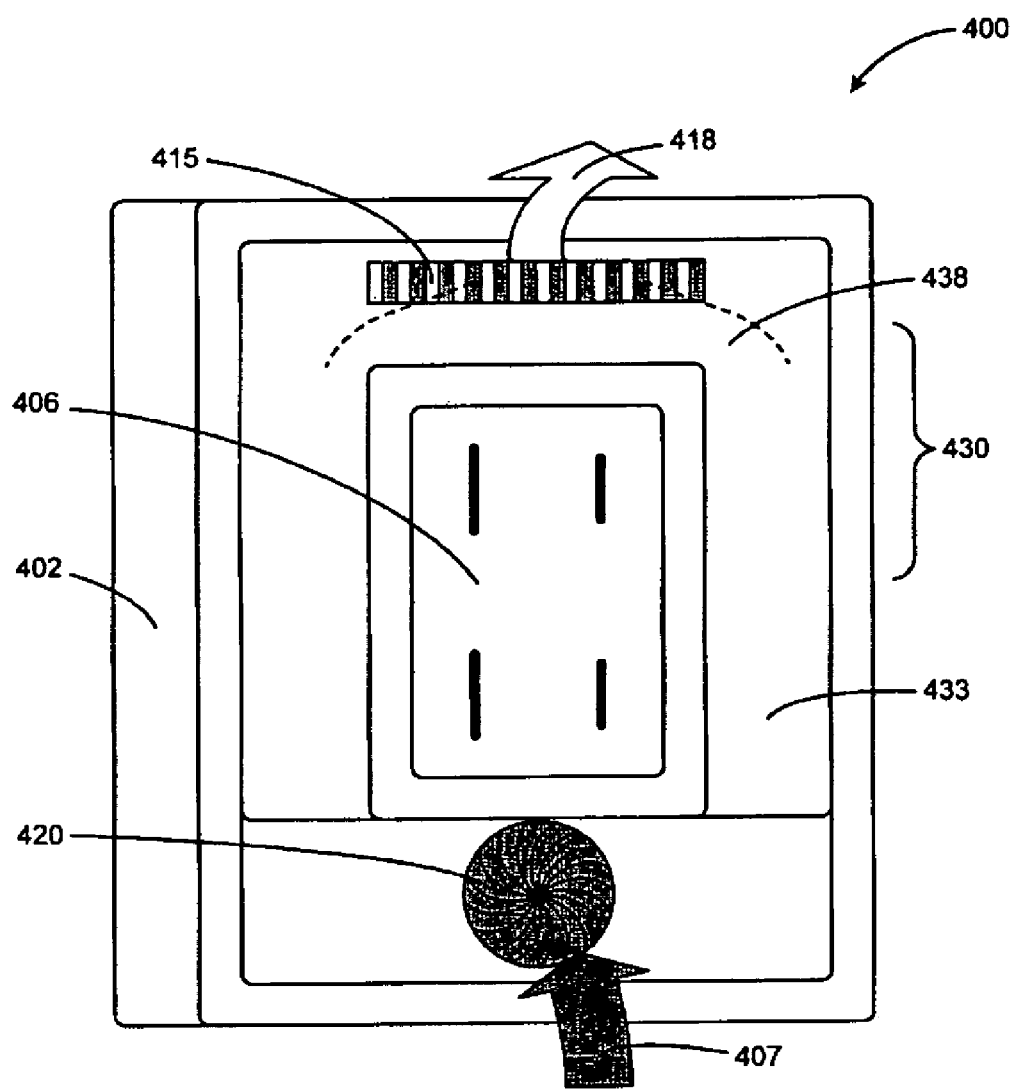
FIG. 4 is an air purifier in accordance with an alternate embodiment of the present invention.

In yet another embodiment of the invention, a air purifier includes a vapor-dispensing module to add scented and/or fragranced vapor to the environment surrounding the air purifier. As illustrated in FIG. 4, an air purifier 400 includes a housing 402, an airflow module 420, one or more plug receptacles 406, an air output 415 for purified air 418, and an air sanitizer module (not shown) similar to housing 202, airflow module 220, plug receptacles 206, air output 215 for purified air 218, and air sanitizer module 210 discussed above, respectively, with reference to FIG. 2.

In accordance with one exemplary embodiment, air purifier 400 includes a vapor-dispensing module 430 similar to vapor-dispensing module 130 discuss above with reference to FIG. 1C. In accordance with an aspect of one exemplary embodiment, vapor-dispensing module 430 includes a reservoir 433 (or other form of air additive component) to store a volatilizable material (e.g., oil, gel, and the like), and one or wicks 438 (or an emanator pad associated therewith, as discussed below). Furthermore, various embodiments of vapor-dispensing module 430 may include an end of use indicator (not shown) to alert a user that reservoir 433 is substantially out of volatilizable material or includes a low level of volatilizable material. In accordance with aspects of one exemplary embodiment, the end of use indicator may be a visual indicator (e.g., a light) and/or an audible indicator (e.g., a continuous or intermittent noise emitted through a speaker).

In operation of one embodiment of air purifier 400, airflow module 420 is configured to move air 407 through, around, or across wick 438 such that air 407 is fragranced before being purified by the air sanitizer module. In this embodiment, the air sanitizer is configured in a manner that will not substantially filter out any fragrance added to air 407. In operation of another embodiment of air purifier 400, airflow module 420 is configured to move purified air 418 through, around, or across wick 438 such that purified air 418 includes a fragrance after being purified by the air sanitizer module so that a fragranced, purified air is output by air output 418. In operation of yet another embodiment of air purifier 400, airflow module 420 is configured to move air 407 through, around, or across a first wick 438 such that air 407 is fragranced before being purified by the air sanitizer module, and is configured to move the purified, fragranced air through, around, or across a second wick 438 after being purified by the air sanitizer module.

Figure 5:
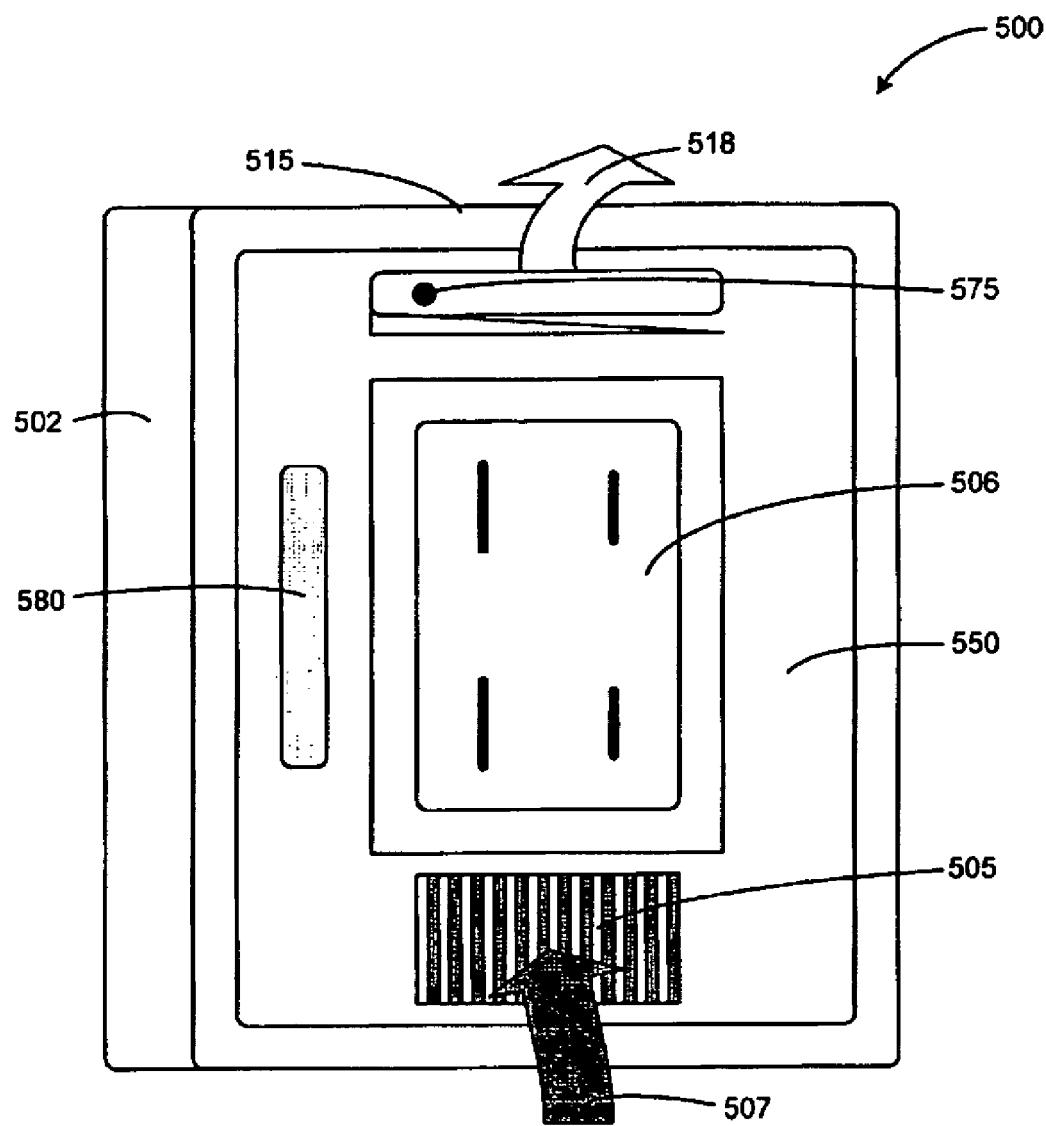
FIG. 5 is an alternate view of the air purifier shown in FIG. 4.

The amount of vapor dispensed by a vapor-dispensing module of one embodiment of an air purifier may be controlled utilizing a controller. An air purifier 500, as shown in FIG. 5, includes a housing 502, one or more plug receptacles 506, an air output 515 for purified air 518, an air sanitizer module (not shown), and a cover 550 providing air intake 505 similar to housing 302, plug receptacles 306, air output 315 for purified air 318, the air sanitizer module, and cover 350 providing air intake 305, respectively, discussed above with respect to FIG. 3. Furthermore, air purifier 500 includes a vapor-dispensing module (not shown) including a reservoir, a wick (or emanator), and/or an end of use indicator similar to vapor-dispensing devices 130 and 430 (including reservoir 433 and wick 438) discussed above with respect to FIGS. 1 and 4, respectively.

In an exemplary embodiment, air purifier 500 also includes a control lever 575 in communication with the vapor-dispensing device. Control lever 575 may be any device, component, or combination of components capable of controlling the rate at which additives, fragrancing, and/or other vapors are introduced into air 507 and/or purified air 518. As such, control level 575 may be any controller known in the art or developed in the future. In accordance with an aspect of one exemplary embodiment of the invention, lever controller 575 is a sliding lever.

Air purifier 500, in another exemplary embodiment, includes a use-up indicator 580 in communication with the reservoir. Use-up indicator 580 may be any device, component, or combination of components suitably configured to display the amount of vapor-releasing substance(s) (e.g., oil, water, gel-based materials, and the like) remaining within the reservoir.

Figure 6:
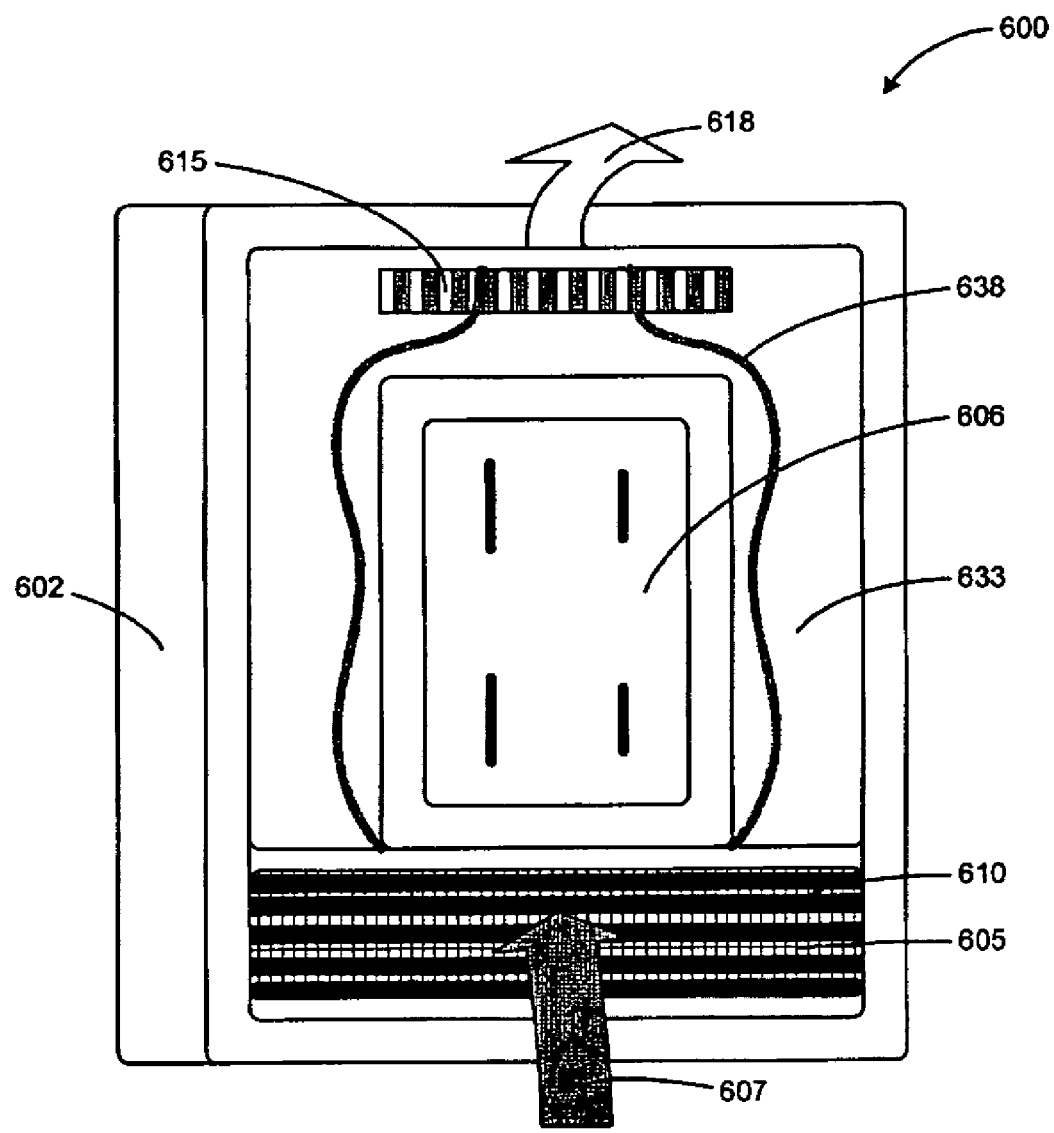
FIG. 6 is a diagram of an air purifier in accordance with an alternate embodiment of the present invention.

Embodiments of a low-profile air purifier 600, as shown in FIG. 6, include a housing 602, one or more plug receptacles 606, and an air output 615 for purified air 618 similar embodiments discussed above with respect to FIGS. 2-5. Air purifier 600, in one exemplary embodiment, includes an air intake 605 and an air sanitizer module 610 similar to air intakes and air sanitizers discussed above. Air intake 605, in accordance with one aspect of the invention, includes vents and apertures to allow air 607 to enter air purifier 600. In another aspect of the invention, air sanitizer module 610 is a filter. In this manner, air intake 605 and air sanitizer module 610 are combined such that as air 607 pass through air intake 605, impurities in air 607 are filtered out.

In another exemplary embodiment, air purifier 600 includes a vapor-dispensing module formed of a reservoir 633 and a wick 638 similar to reservoir 433 and wick 438 discussed above with respect to FIG. 4. In accordance with an aspect of one exemplary embodiment of the invention, reservoir 433 and/or wick 438 may be configured to be a removable refill for air purifier 600. Notably, the invention contemplates that air purifier 600 may also include a fan or other airflow module (not shown) to facilitate movement of air 607 and/or purified air 618 into, within, and/or out of air purifier 600.

Figure 7B:
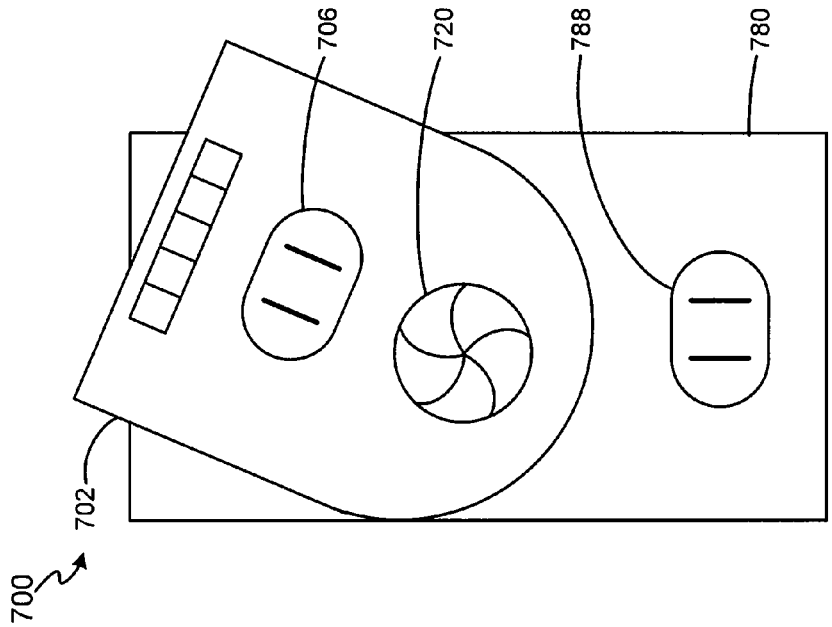
FIGS. 7A and 7B are diagrams of one embodiment of an air purifier capable of rotating around an axis normal to a front surface of an electrical outlet.
Figure 7A:
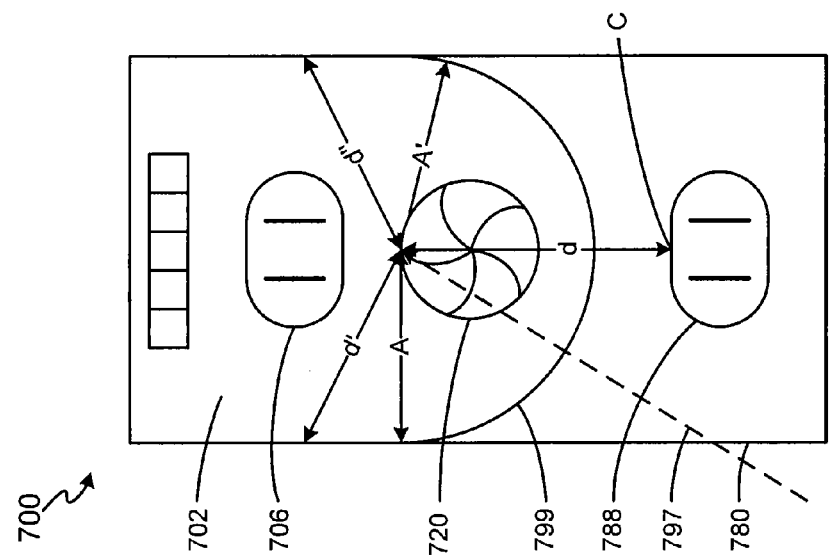

Another embodiment of the invention includes a low-profile air purifier capable of rotating on an axis normal to an electrical outlet. For example, in FIG. 7A an air purifier 700 including a housing 702, one or more plug receptacles 706, an airflow module 720 and/or an air intake (not shown), and an air sanitizer module (not shown) similar to embodiments discussed above is illustrated. Housing 702, in various embodiments, is configured to rotate within a range of rotational angles. The axis of rotation passes through substantially a center of an electrical receptacle (not shown) with which air purifier 700 is attached. Furthermore, housing 702 includes a perimeter 797 having a curved edge profile 799 with a radius of curvature (i.e., the curvature from A to A'). In an aspect of one exemplary embodiment of the invention, the radius of curvature of curved edge profile 799 is in the range of about 3 cm to about 7 cm. In another exemplary embodiment, housing 702 is configured such that it is capable of rotating about 270 degrees without occluding an electrical receptacle 788 of an electrical outlet 780 with which air purifier 700 is attached (see, for example, FIG. 7B). In other words, housing 702 may be configured such that the distance (d' or d") from the substantial center of the electrical receptacle with which air purifier 700 is attached to pre-determined points on perimeter 797 is less than a distance (d) from the substantial center of the electrical receptacle with which air purifier 700 is attached to a point (C) of electrical receptacle 788.

Figure 8:
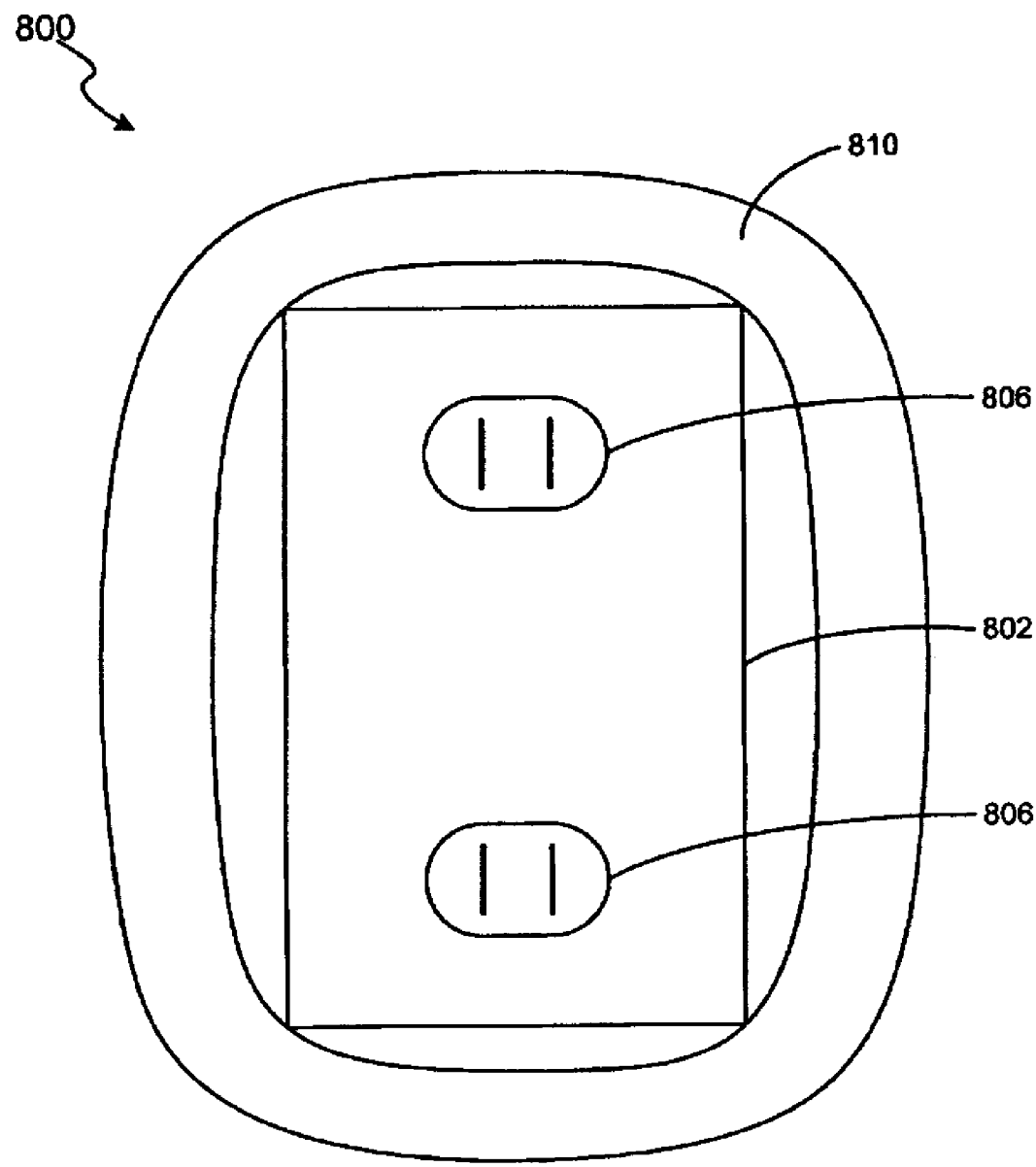
FIG. 8 is a diagram of an embodiment of an air purifier including a rotational air sanitizer module.

Other embodiments of the invention include a low-profile air purifier that purifies the air utilizing a rotating air sanitizer module. An air purifier 800, as illustrated in FIG. 8, according to these embodiments includes a housing 802 and one or more plug receptacles 806 similar to embodiments discussed above in addition to a rotational air sanitizer module 810.

In one exemplary embodiment, air sanitizer module 810 includes a filter similar to filter embodiments discussed above. Furthermore, air sanitizer module 810 is configured to rotate around housing 802. As air sanitizer 810 rotates, air pass over/through air sanitizer module 810 and any unwanted particles and/or particulates are trapped within the filter of air sanitizer module 810.

Referring to FIGS. 9A-9E, a rotatable air purifier 1500 according to various exemplary embodiments of the invention is illustrated. Air purifier 1500, in one exemplary embodiment, includes a housing 1502 to least partially house an air sanitizer module (not shown), a vapor-dispensing module (not shown), and an airflow module 1520 similar to embodiments of air sanitizer modules, vapor-dispensing modules, and airflow modules discussed above, respectively. Furthermore, housing 1502 is suitably configured to rotate about a plug receptacle 1506 included within an anterior surface 1501 of housing 1502, wherein plug receptacle 1506 are similar to embodiments plug receptacles discussed above. Housing 1502, in accordance with an exemplary embodiment of the invention, is configured to rotate around plug receptacle 1506 on an axis normal to an electrical outlet 1580. In an aspect of one exemplary embodiment of the invention, housing 1502 is configured to rotate 360 degrees around plug receptacle 1506 as illustrated in FIGS. 9A, 9B, 9C, and 9D.

Figure 9:
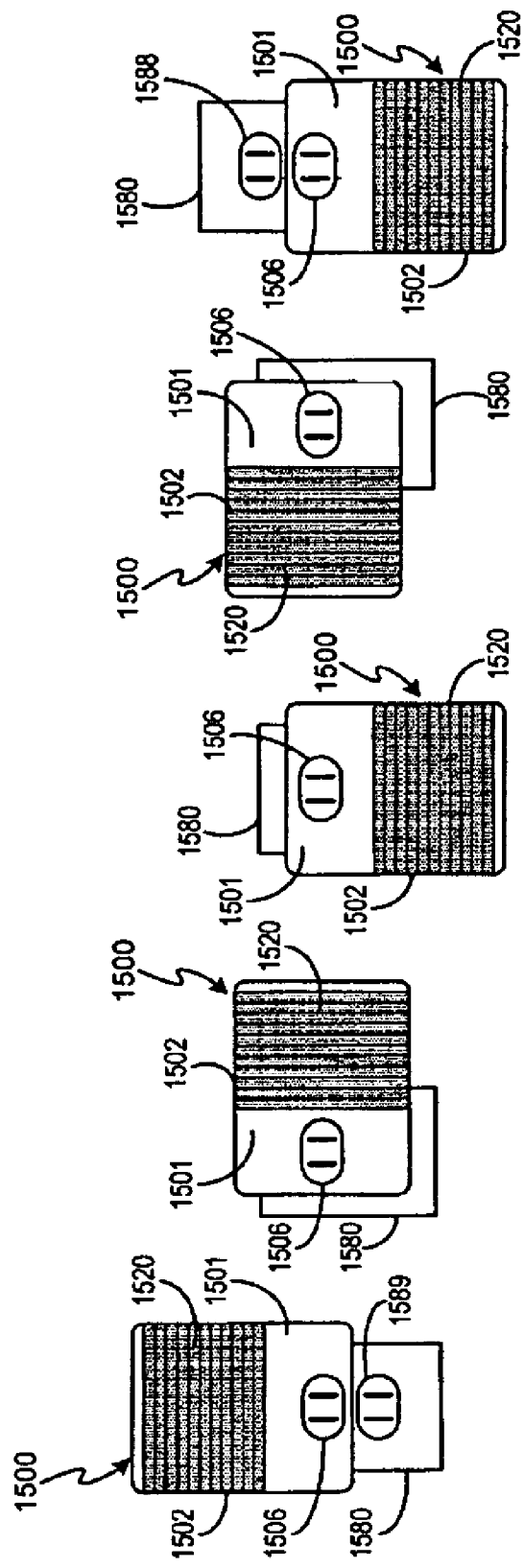
FIGS. 9A-9E are diagrams of one embodiment of an air purifier including a rotational housing.

In another exemplary embodiment of the invention, plug receptacle 1506 is configured not to rotate and/or move when housing 1502 is rotated. In other words, plug receptacle 1506 is configured to remain static such that a plug may be inserted in its traditional upright manner. Moreover, in one embodiment, plug receptacle 1506 is connected to electrical plugs (not shown) extending from a posterior surface (not shown) of air purifier 1500. In accordance with an aspect of one exemplary embodiment of the invention, plug receptacle 1506 and the electrical plugs are configured to remain in place while housing 1502 is rotated around them. FIGS. 9A-9D illustrate air purifier 1500 attached to a top electrical receptacle 1588 (shown in FIG. 9E) of electrical outlet 1580 and include positions wherein electrical receptacle 1588 is not completely or substantially occluded by air purifier 1500, FIG. 9E illustrates that air purifier 1500 may likewise be attached to a bottom electrical receptacle 1589 (shown in FIG. 9A) of electrical outlet 1580 and include positions wherein electrical receptacle 1589 is not completely or substantially occluded by air purifier 1500. Notably, as shown in FIGS. 9A-9E, air purifier 1500 is capable of functioning properly when attached "upside-down", "side ways", "right side-up", and/or anywhere in between to electrical outlet 1580.

Figure 10:
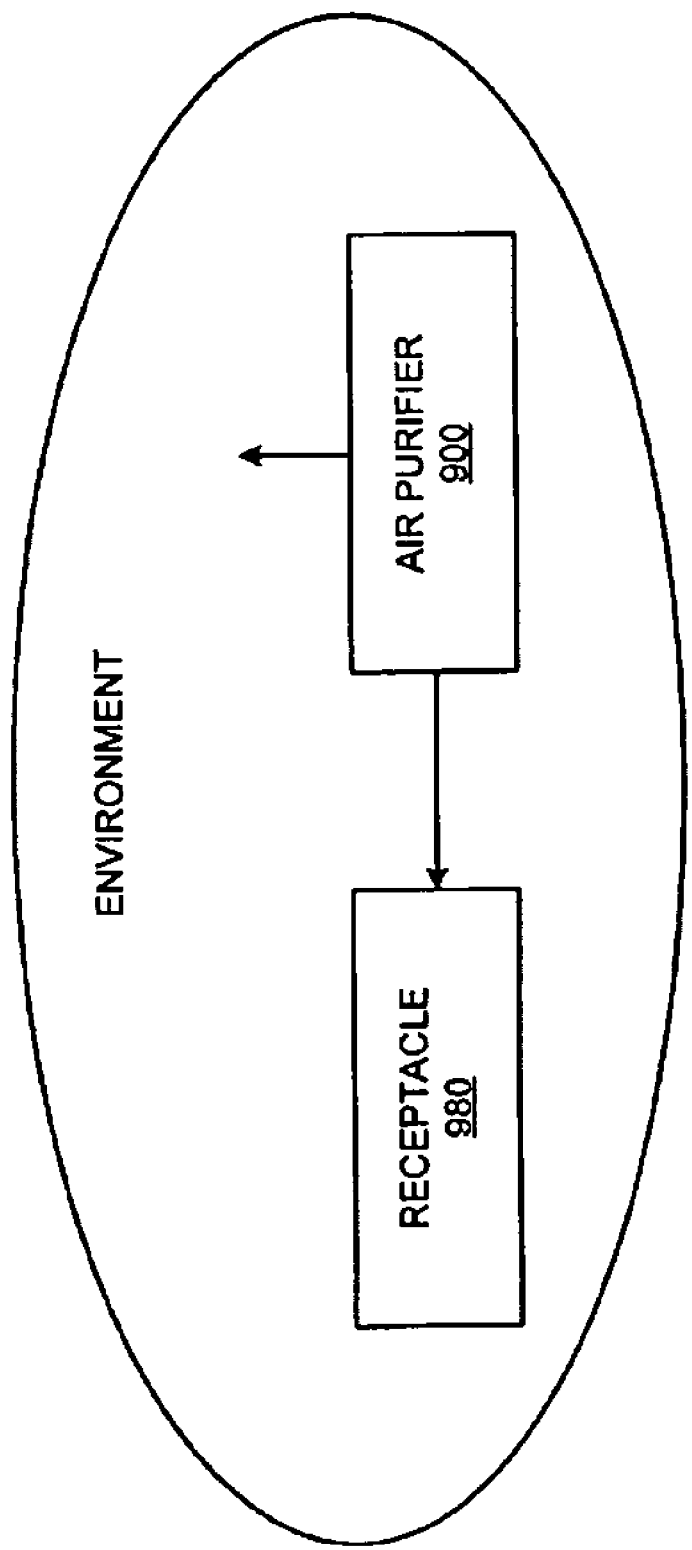
FIG. 10 is a schematic overview of a system providing a context in which the present invention may be practiced.

FIG. 10 is a block diagram of an air purifier 900 generally interfacing with an electrical outlet 980 within an environment. Air purifier 900 may include any suitable device, component, or combination of components suitably configured to alter the environment in some manner such as, for example, altering its aromatic vapor density and/or by purifying the ambient air. In accordance with another embodiment, a refill may be included as a portion of air purifier 900, wherein the refill includes air filtration and/or fragrance elements configured to be replaced at substantially the same time. Notably, air purifier may be any of air purifiers 100, 200, 300, 400, 500, 606, 700, 800, or 1500.

In accordance with yet another embodiment of the present invention, air purifier 900 is configured to give the appearance that it is something other than an air purifier. For example, the air purifier may be configured to mimic an electrical receptacle having an outlet pattern (discussed in greater detail below). In this embodiment, air purifier 900 has a front surface which includes an outlet pattern substantially corresponding to the outlet pattern of the receptacle, and a plug configured to interface with the electrical receptacle.

For example, FIG. 11 illustrates air purifier 900 interfacing with an electrical outlet 980 through one or more plugs (or other interface structures) 978 corresponding to an outlet pattern 983. Electrical outlet 980 may be any device, component, or combination of components suitable for providing electrical current to air purifier 900. For example, electrical outlet 980 may be a standard wall outlet (duplex), a power strip, or a quadplex.

Air purifier 900 includes a front surface 909 (which may or may not be planar) that includes one or more plug receptacles 906 which substantially corresponds to outlet pattern 983 of electrical outlet 980. In addition, air purifier 900 is generally configured to removeably attach to receptacle outlet 980.

An assembly 912 is configured to modify one or more attributes of the environment as described above such as, for example, purifying and, optionally, fragrancing the air in the environment. In this regard, assembly 912 is used herein to collectively refer to the various components depicted in FIGS. 1A-1C (e.g., sanitizer module 110, air module 120, and/or vapor dispensing module 130).

Assembly 912 is suitably interposed between (and/or to the side of) front surface 909 and plug receptacles 906. In an embodiment wherein assembly 912 corresponds includes a vapor dispensing device, it may also include one or more components (e.g., wicks, capillary tubes, and the like) which provide a means for transporting volatilizable material from one location to another (e.g., from a reservoir to an evaporation pad or emanator), and/or one or more components (e.g., emanator pads, secondary wicks, and the like) which provide a surface or surfaces from which the transported material undergoes mass transfer or evaporation to a surrounding environment.

Notably, it is advantageous to utilize electrical outlet 980 as a power source to provide any electrical functionality required by air purifier 900. For example, the fragrance delivery device may include one or more emanators or heating elements designed to control the rate at which the volatilizable material evaporates into the environment. In such a case, assembly 912 may include various terminals, wires, conductive traces, plugs, and other such components facilitating interface and power delivery from electrical outlet 980. In a particularly preferred embodiment, for example, assembly 912 includes a resistive heating element that is thermally coupled to an emanator pad or wick which communicates with a volatilizable material.

Although air purifier 900 is illustrated as generally rectilinear in cross-section, it may in fact include any number of discrete or integrated housings having any arbitrary shape. Furthermore, in accordance with this embodiment, it is not necessary for air purifier 900 to exhibit a geometry which is similar in size or shape to that of electrical outlet 980 or any face-plates provided in conjunction with electrical outlet 980. That is, as shown in FIG. 12, air purifier 900 may actually be smaller than an electrical outlet 980 (e.g., on the order of the size of plug receptacles 906). Similarly, as shown in FIG. 13, air purifier 900 may be asymmetrical with respect to electrical outlet 980 and/or any plug receptacles 906 provided in electrical outlet 980. As shown in FIG. 13, for example, the lower boundary of front face 909 may extend below (or above) electrical outlet 980.

Figure 17:
FIG. 17 is a diagram illustrating a variety of exemplary receptacle and outlet configurations.

FIG. 14 shows a general configuration for electrical outlet 980 which includes an outer boundary and/or faceplate perimeter 983 along with one or more outlets 988. Outlets 983 may exhibit any suitable shape, and may include any suitable combination of male, female, or other connection types. For example, referring now to FIG. 15, electrical outlet 980 may consist of a conventional dual-outlet power receptacle including a pair of two-prong outlets 988 and a faceplate perimeter 983. Similarly, as shown in FIG. 16, electrical outlet 980 may consist of a conventional quad-outlet power receptacle including four two-prong outlets 988 and a faceplate perimeter 983. FIG. 17 presents a matrix of additional standard receptacle designs with which the present invention may be employed. Note also that the present invention may be used in connection with ground-fault interrupt (GFI) electrical outlets.

It will be appreciated that the present invention is not limited to electrical receptacles. Indeed, electrical outlet 980 may comprise any suitable structure configured to provide electricity, data, or any other power and/or information source to air purifier 900 through a suitable interface. For example, suitable receptacles include RJ-11 and RJ-45 jacks used in connection with high-speed data transfer (and analog telephone communication), co-axial connectors used in connection with electrical and optical cable networks, and any other receptacle design now known or developed in the future.

To achieve the goal of appearing to be something other than a vapor-dispensing device, air purifier 900 may be designed to mimic not only an electrical receptacle, but any number of other objects which might typically appear in the target environment. For example, the vapor-dispensing device might be configured to mimic a wall switch, a multi-outlet power strip, a night-light, or any other suitable object.

As mentioned above, discreetness of the environment-altering device may also be achieved by configuring the device such that it blends in with its environment. This blending may be accomplished, for example, by including a housing configured such that a cross-section orthogonal to and through the perimeter of the housing defines a blending contour from the front surface to the wall outside the perimeter of the electrical receptacle.

Figure 18:
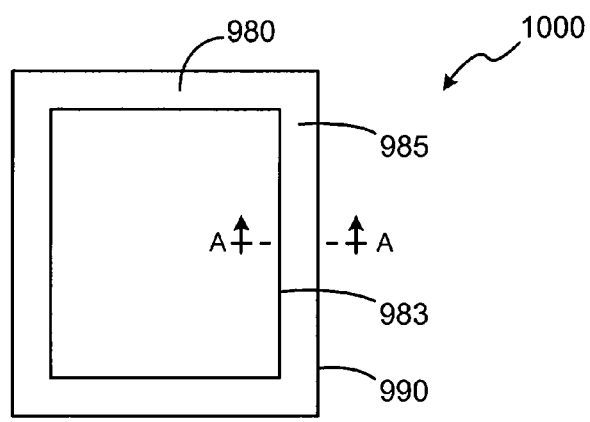
FIG. 18 is a diagram of an exemplary vapor dispensing device.

Referring to FIG. 18, for example, electrical outlet 980 includes a faceplate perimeter 983, which may or may not be rectangular as illustrated. Faceplate perimeter 983 generally fits against or flush with a wall 1000. A housing 985 has a perimeter 990 (which need not be rectangular, and need not correspond to the shape of faceplate perimeter 983) that is characterized by a cross-section 'A' as shown, wherein the cross-section defines a blending-contour with respect to wall 1000, thus providing added discreetness.

Figure 19:
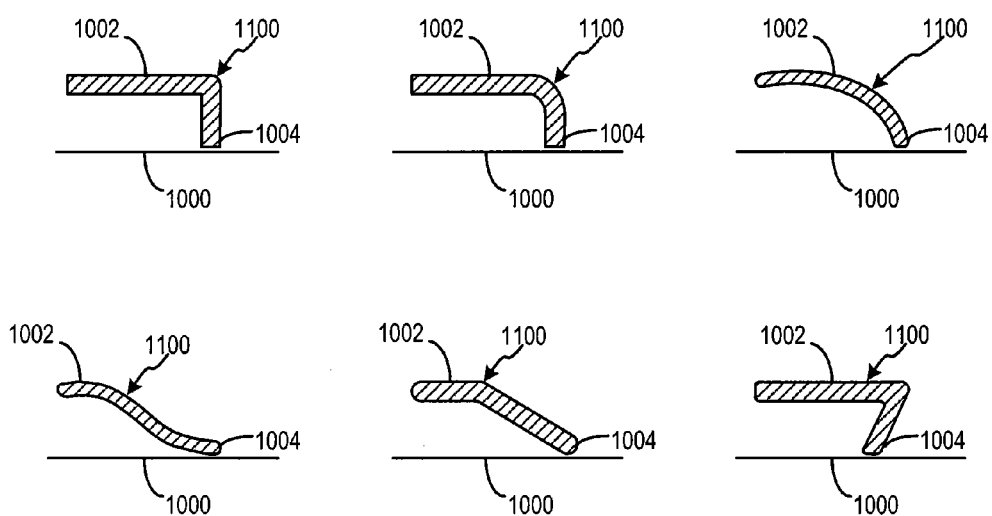
FIG. 19 shows diagrams of various cross-section diagrams defining blending contours.

More particularly, referring to FIG. 18 in connection with the six example cross-sections illustrated in FIG. 19, a cross-section 1100 near the perimeter 990 of housing 985 forms a blending-contour between a front 1002 and wall 1000. In general, a blending-contour forms a continuous (but not necessarily smooth or differentiable) curve extending from the front 1002 of housing 985 to a terminus 1004 near or in contact with wall 1000. It will be appreciated that the exemplary shapes shown in FIG. 19 do not exhaust the range of blending-contour shapes that may be used in accordance with the present invention.

In accordance with a further aspect of the present invention, air purifier 900 blends in with its environment by including at least two antipodal points on the perimeter of housing 985 make contact with wall 1000 outside a housing perimeter 1102 of faceplate perimeter 983 when air purifier 900 is connected to electrical outlet 980.

Figure 22:
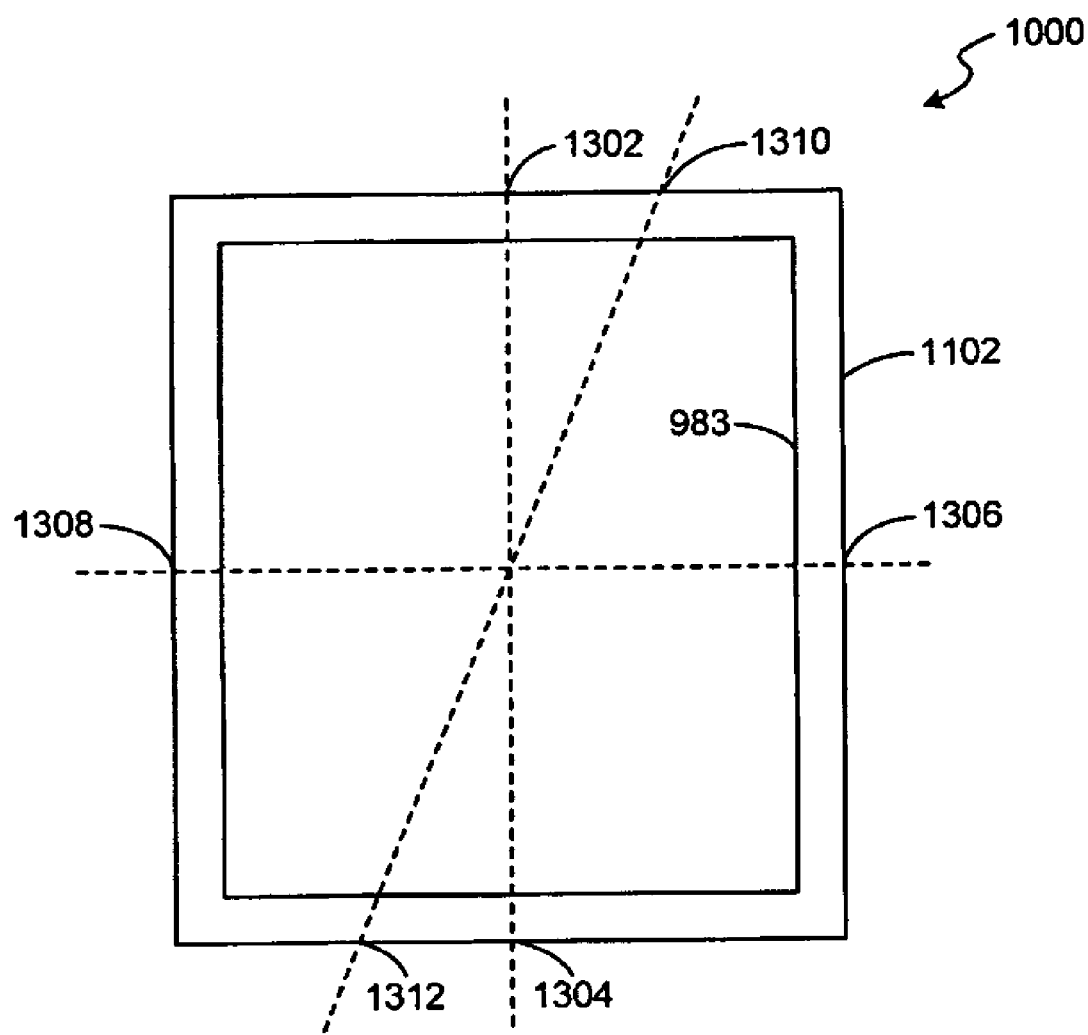
FIG. 22 is a diagram of exemplary vapor-dispensing device symmetries.

Referring to FIG. 22, housing perimeter 1102 is configured such that at least two points on opposite sides of housing perimeter 1102 make contact with wall 1000 outside of faceplate perimeter 983. For example, housing perimeter 1102 may make contact with wall 1000 at one or more of the following pairs of points: points 1302 and 1304; points 1306 and 1308; and points 1310 and 1312. The word "point" is used in the sense of a location, and need not correspond to a small circular contact point; indeed, any arbitrary contact region (or closely situated regions) may be considered a "point" as that term is used in connection with this embodiment.

Figure 23:
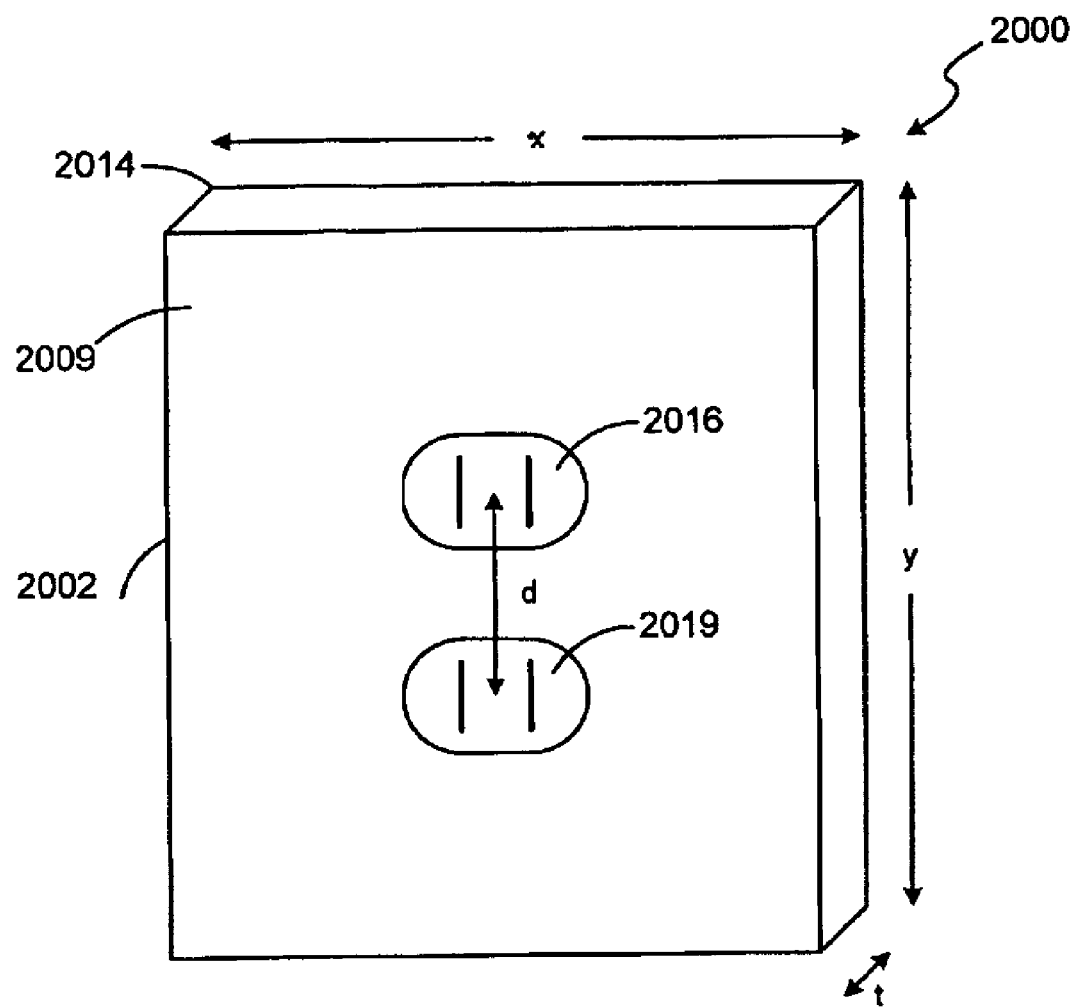
FIG. 23 is a diagram illustrating an isometric view of exemplary vapor-dispensing device geometries.

In accordance with a further aspect of the present invention, an air purifier has low-profile dimensions. More particularly, referring now to FIG. 23, an air purifier 2000 includes a housing 2002 having a front surface 2009 and a back surface 2014 separated by a thickness t, wherein back surface 2014 has a minor axis dimension x and a major axis dimension y. A first device outlet 2016 and a second device outlet 2019 are provided on the front surface 2009 of housing 2002. The device outlets 2016 and 2019 are separated by an inter-outlet distance d; wherein: x/d is between approximately 2.0 and 2.5, preferably about 2.125, y/d is between approximately 3.0 and 3.5, preferably about 3.25, and t/d is between approximately 0.5 and 1.0, preferably about 0.625. In accordance with yet a further aspect of the present invention, the thickness t is less than approximately 20 percent of the major axis dimension y.

To achieve the goal of blending in with the environment, any number of other attributes of the device may be designed to match or be thematically consistent with one or more attributes of the environment. For example, the color, texture, and/or geometry of air purifier 2000 may be selected to better blend in with the wall, furniture, and/or other components of the environment.

Discreetness of air purifier 2000 may also be achieved by configuring the device such that it covers all or a portion of the electrical receptacle. In accordance with one aspect of the present invention, for example, air purifier 2000 substantially covers the receptacle by including a housing whose perimeter substantially encompasses the perimeter of the electrical receptacle's faceplate when the vapor-dispensing device is connected to the electrical receptacle.

More particularly, referring to the four exemplary configurations shown in FIG. 20, faceplate perimeter 983 (or, alternatively, receptacle perimeter) is substantially encompassed by housing perimeter 1102. That is, housing perimeter 1102 may fully encompass faceplate perimeter 983 such that all points on faceplate perimeter 983 fall within the area defined by housing perimeter 1102 (as shown in FIGS. 20A and 20D) or so that a portion of faceplate perimeter 983 lies at the border of (or indeed, slightly outside of) housing perimeter 1102 (as shown in FIGS. 20B and 20C). While the illustrated faceplates and housings shown in FIG. 20 are generally rectangular and generally correspond to each other, the faceplates and housings may have any variety of shapes, and it is not necessary for the shapes to generally correspond to each other. For example, faceplate perimeter 983 may be rectangular while housing perimeter 1102 is circular or elliptical. In accordance with a further aspect of the present invention, a vapor-dispensing device includes a housing whose aspect ratio is substantially similar to the aspect ratio of a receptacle faceplate, and whose center is substantially coincident with the center of the faceplate.

Figure 21:
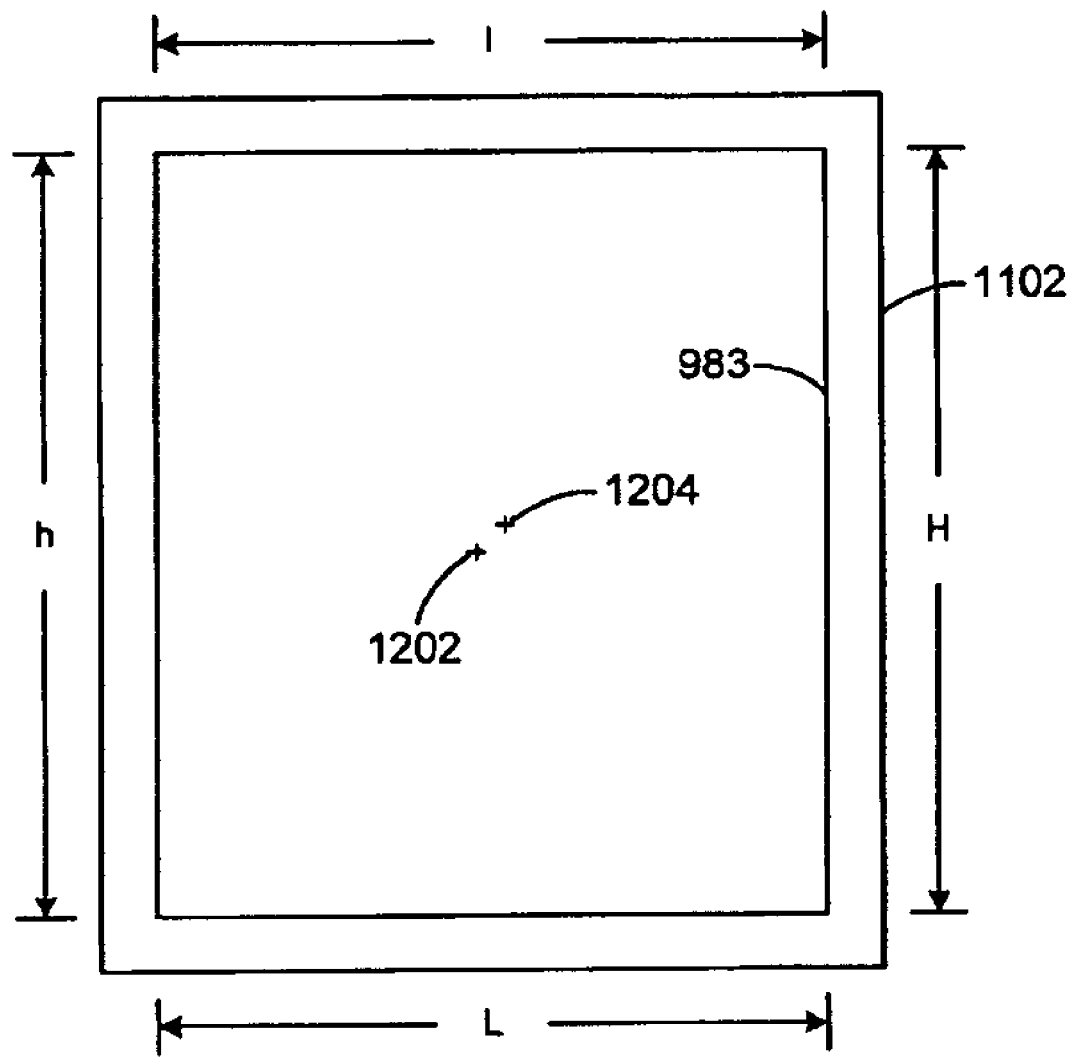
FIG. 21 is a diagram of exemplary vapor-dispensing device geometries.

Referring to FIG. 21, faceplate perimeter 983 is characterized by a center (or centroid) 1202 and height and length dimensions h and l respectively. Similarly, housing perimeter 1102 is characterized by a center (or centroid) 1204 and height and length dimensions H and L respectively. Faceplate perimeter 983 has an aspect ratio defined as H/L, and housing perimeter 1102 has an aspect ratio defined as h/l. In accordance with one aspect of the present invention, center 1202 substantially coincides with center 1204. In accordance with a further aspect of the present invention, the aspect ratio of faceplate perimeter 983 is substantially equal to the aspect ratio of housing perimeter 1102. In one embodiment, for example, the faceplate aspect ratio is substantially equal to the aspect ratio of a standard dual-outlet faceplate such as, for example, between approximately 1.3 and 1.7, and preferably about 1.5. It will be appreciated that the aspect ratio may be defined in any convenient matter depending upon the shape of the respective faceplate and housing.

Although the invention has been described herein in conjunction with the appended drawings, those skilled in the art will appreciate that the scope of the invention is not so limited. Modifications in the selection, design, and arrangement of the various components and steps discussed herein may be made without departing from the scope of the invention.

We claim:

1. An air purifier configured to engage an electrical outlet, the electrical outlet having a first electrical receptacle pattern comprising a first electrical receptacle, the air purifier comprising a housing comprising:
an anterior surface having a second electrical receptacle pattern, said second electrical pattern comprising a second electrical receptacle, said second electrical pattern substantially corresponding to the first electrical receptacle pattern;
a posterior surface comprising a plug pattern, said plug pattern comprising at least one plug; and
a device interposed between said anterior surface and said posterior surface, said device comprising an airflow module configured to facilitate the movement of air and said device configured to
intake air,
purify said air, and
output said purified air,
wherein the air purifier is configured to mimic an electrical outlet.

2. The air purifier of claim 1, said device comprising:
an air intake;
an air sanitizer module in communication with said air intake, wherein said air sanitizer module is configured to purify air from said air intake; and
an air output in communication with said air sanitizer module, wherein said air output is configured to output said purified air.

3. The air purifier of claim 2, wherein said
airflow module is in communication with said air intake, said air sanitizer module, and said air output; and wherein said airflow module is configured to facilitate movement of said air from said air intake to said air sanitizer module, and said purified air from said air sanitizer module to said air output.

4. The air purifier of claim 3, wherein said airflow module is one of a fan, a micro fan, a squirrel cage fan, a cross-flow fan, an ionization device, and a pump.

5. The air purifier of claim 2, wherein said air sanitizer module is configured to address the presence of one of a germ, an allergen, and a malodor.

6. The air purifier of claim 5, said air sanitizer module comprising one of a filter, a chemical absorbent material, an ultraviolet device, an ozonation device, and an ionization air sanitation device.

7. The air purifier of claim 2, wherein said device is configured to evenly distribute said air across said air sanitizer module.

8. The air purifier of claim 3, said device further comprising:
a vapor-dispensing module in communication with said airflow module, wherein said vapor-dispensing module is configured to add a fragrance to one of said air and said purified air.

9. The air purifier of claim 8, said vapor-dispensing module comprising:
a reservoir configured to store a volatilizable material; and
one of a wick, an emanator pad, a heating element, and a capillary tube in communication with said reservoir.

10. The air purifier of claim 8, wherein said vapor-dispensing module and said air sanitizer module comprise a refill portion of the air purifier.

11. The air purifier of claim 1, the first electrical pattern further comprising a third electrical receptacle; and said housing further comprising an edge profile comprising a radius of curvature, wherein said housing is configured such that a first distance from said substantial center of the first electrical receptacle to said edge profile is less than a distance from said substantial center of the first electrical receptacle to a point of said third electrical receptacle closest to said substantial center of the first electrical receptacle.

12. The air purifier of claim 11, said edge profile comprising a radius of curvature in the range of about 3 centimeters (cm) to about 7 cm.

13. An air purifier, comprising:
a housing comprising an anterior surface, said anterior surface comprising an electrical plug receptacle, said electrical plug receptacle coupled to electrical plugs extending from a posterior surface of said air purifier;
an air sanitizer module housed substantially within said housing, wherein said air sanitizer module comprises an airflow module, said air sanitizer module is configured to at least partially purify air, and said housing is configured to rotate about said electrical receptacle and electrical plugs when said electrical plugs are attached to an electrical outlet; and
a vapor dispensing module in communication with said airflow module, wherein said vapor-dispensing module is configured to add a fragrance to said air.

14. The air purifier of claim 13, wherein said
airflow module is housed substantially within said housing, wherein said airflow module is configured to facilitate at least one of movement of said air into said air purifier, movement of said air within said air purifier, and movement of said air out of said air purifier.

15. The air purifier of claim 13, wherein said electrical receptacle and electrical plugs are each configured to be static.

* * * * *